US009782339B2

(12) United States Patent
Chopra et al.

(10) Patent No.: US 9,782,339 B2
(45) **Date of Patent: *Oct. 10, 2017**

(54) ORAL CARE COMPOSITIONS

(71) Applicant: Colgate-Palmolive Company, New York, NY (US)

(72) Inventors: Suman Chopra, Monroe, NJ (US); Dennis Ontumi, Easton, PA (US); Prakasarao Mandadi, Flemington, NJ (US); Venda Maloney, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/293,691

(22) Filed: Oct. 14, 2016

(65) Prior Publication Data

US 2017/0027847 A1 Feb. 2, 2017

Related U.S. Application Data

(63) Continuation of application No. 14/868,469, filed on Sep. 29, 2015, now Pat. No. 9,498,425, which is a continuation of application No. 13/997,430, filed as application No. PCT/US2011/038874 on Jun. 2, 2011, now Pat. No. 9,174,070, which is a continuation-in-part of application No. PCT/US2010/061711, filed on Dec. 22, 2010.

(51) Int. Cl.

| | |
|---|---|
| ***A61Q 11/00*** | (2006.01) |
| ***A61K 8/81*** | (2006.01) |
| ***A61K 8/22*** | (2006.01) |
| ***A61K 8/24*** | (2006.01) |
| ***A61K 8/86*** | (2006.01) |
| ***A61K 8/90*** | (2006.01) |
| ***A61K 8/02*** | (2006.01) |
| ***A61K 8/34*** | (2006.01) |

(52) U.S. Cl.

CPC .......... *A61K 8/8182* (2013.01); *A61K 8/0216* (2013.01); *A61K 8/22* (2013.01); *A61K 8/24* (2013.01); *A61K 8/345* (2013.01); *A61K 8/8176* (2013.01); *A61K 8/86* (2013.01); *A61K 8/90* (2013.01); *A61Q 11/00* (2013.01); *A61K 2800/28* (2013.01); *A61K 2800/52* (2013.01); *A61K 2800/57* (2013.01); *A61K 2800/87* (2013.01)

(58) Field of Classification Search

CPC ...... A61K 8/8176; A61K 8/90; A61K 8/0216; A61K 8/345; A61K 8/86; A61K 8/24; A61K 8/22; A61K 8/8182; A61Q 11/00

See application file for complete search history.

(56) References Cited

U.S. PATENT DOCUMENTS

| | | | | |
|---|---|---|---|---|
| 5,122,370 | A | 6/1992 | Merianos et al. | |
| 5,171,564 | A | 12/1992 | Nathoo et al. | |
| 5,776,435 | A | 7/1998 | Gaffar et al. | |
| 5,945,032 | A * | 8/1999 | Breitenbach | A01N 59/00 252/186.29 |
| 8,540,971 | B2 * | 9/2013 | Zaidel | A61K 8/0208 424/401 |
| 9,174,070 | B2 * | 11/2015 | Chopra | A61K 8/22 |
| 2005/0036956 | A1 | 2/2005 | Fei et al. | |
| 2005/0038181 | A1 | 2/2005 | Chopra et al. | |
| 2006/0045854 | A1 * | 3/2006 | Zaidel | A61K 8/0208 424/53 |
| 2006/0062744 | A1 | 3/2006 | Lokken | |
| 2007/0071695 | A1 * | 3/2007 | Chopra | A61K 8/20 424/53 |
| 2007/0071696 | A1 * | 3/2007 | Wang | A61K 8/20 424/53 |
| 2010/0135931 | A1 | 6/2010 | Baig et al. | |

FOREIGN PATENT DOCUMENTS

| | | |
|---|---|---|
| CA | 2484372 | 3/2006 |
| EP | 0868903 | 10/1998 |
| JP | 2007-518733 | 7/2007 |
| WO | WO 97/11675 | 4/1997 |
| WO | WO 2007/037961 | 4/2007 |

OTHER PUBLICATIONS

Anonymous, "Peroxydone XL-1 0," 2016, Retrieved from the Internet: http://cosmetics.specialchem.com/product/i-ashalnd-specialty-chemical-peroxydone-xl-10. Retrieved on Feb. 18, 2016.

Anonymous, "Polyplasdone crospovidone superdisintegrants," 2013, Retrieved from the Internet. http://www..ashland.com/Ashland/Static/Documents/ASI/PC11319_Polyplasdone_Overview.pdf, Retrieved on Feb. 18, 2016.

* cited by examiner

*Primary Examiner* — Blessing M Fubara

(57) ABSTRACT

Described herein are oral care compositions comprising a crosslinked polyvinylpyrrolidone complexed with hydrogen peroxide, together with particular co-polymers as additional excipients; including some embodiments which further comprise a calcium abrasive.

11 Claims, No Drawings

ORAL CARE COMPOSITIONS

CROSS-REFERENCE TO RELATED APPLICATIONS

This application is a continuation of U.S. patent application Ser. No. 14/868,469, filed Sep. 29, 2015, now allowed, which is a continuation U.S. patent application Ser. No. 13/997,430, filed Jun. 24, 2013, now U.S. Pat. No. 9,174,070, which is a national stage entry under 35 U.S.C. §371 of International Patent Application No. PCT/US2011/038874, filed Jun. 2, 2011, which is a continuation-in-part of International Patent Application No. PCT/US2010/061711, filed Dec. 22, 2010, the contents of which are hereby incorporated by reference in their entirety.

BACKGROUND

Dentifrice formulations comprising peroxide are known and useful for cleaning and whitening teeth. The peroxide can bleach the teeth, remove stains, and kill cariogenic bacteria. However, peroxide compounds are highly reactive, and consequently difficult to formulate. Moreover, hydrogen peroxide can spontaneously decompose to form oxygen gas ($O_2$) and water, so that on storage, the dentifrice containers may bloat, burst or leak, and the remaining formulation will not have enough peroxide remaining to clean and whiten teeth effectively. Some initially comprise very high levels of peroxide, which decomposes over time, so that the exact amount of peroxide delivered on application is variable and largely depends on how long and under what conditions the dentifrice has been stored.

Abrasives comprising calcium phosphate salts, such as calcium pyrophosphate, dicalcium orthophosphate dihydrate, tricalcium phosphate, and calcium polymetaphosphate are useful in dentifrice materials, as in addition to providing an abrasive action which cleans the teeth, such salts provide a source of calcium and phosphate which can help build and repair the teeth. Calcium salts such as calcium carbonate are also commonly used as abrasives. However, under oxidizing conditions, calcium ions can readily form calcium peroxide ($CaO_2$) and calcium oxide (CaO, also known as quicklime), which is highly reactive and corrosive, reacting exothermically with water for example to form calcium hydroxide ($Ca(OH)_2$). Thus dentifrices using calcium salts are not preferred for formulation with peroxide.

Abrasive-free dentifrices comprising peroxide also present formulation challenges. While the problem with interaction with the abrasive is removed, the peroxide may still react with other components of the formulation and/or decompose to release $O_2$.

By exposure to aqueous environments, as in the oral cavity, the PVP-$H_2O_2$ dissociates into individual species (PVP polymer and $H_2O_2$). The PVP-$H_2O_2$ complex is generally comprised of about 80% by weight polyvinyl pyrrolidone and 20% by weight $H_2O_2$. Single phase whitening dentifrice compounds comprising PVP-$H_2O_2$ complexes are described, e.g., in WO/2007/037961, and its parent US Pub. No. US 2007-0071695 A1, the contents of which are incorporated herein by reference.

While there are numerous publications of gels comprising peroxide, such gels are generally for use with dental trays or strips, rather than for application using a toothbrush, and such gels are not necessarily suitable for use as a dentifrice because they may adhere to the toothbrush, rather than rinsing off easily, and leave the consumer with an unpleasant experience due to the lack of foaming provided by the product.

There is thus a need for improved peroxide dentifrice formulations that are stable for long-term storage and are suitable for everyday consumer use.

SUMMARY

In some embodiments, the present invention provides oral care compositions that are stable during long term storage and remain effective to clean and whiten teeth. In some embodiments, the invention provides an oral care composition comprising: (i) a crosslinked polyvinylpyrrolidone complexed with hydrogen peroxide and (ii) an abrasive. In some embodiments, the abrasive is a calcium abrasive. In other embodiments, the invention provides an oral care composition comprising a crosslinked polyvinylpyrrolidone complexed with hydrogen peroxide, and a stabilizing amount of additional linear and/or crosslinked polyvinylpyrrolidone. In further embodiments, the invention provides an oral care composition comprising (i) a crosslinked polyvinylpyrrolidone complexed with hydrogen peroxide, and an ethylene oxide, propylene oxide block co-polymer of formula (ethylene oxide)$_x$-(propylene oxide)$_y$ wherein x is an integer of 80-150 and y is an integer 30-80, having an average molecular weight of greater than 5000 Da. Further embodiments of the invention will be apparent from the detailed description and the examples.

DETAILED DESCRIPTION

As used throughout, ranges are used as shorthand for describing each and every value that is within the range. Any value within the range can be selected as the terminus of the range.

All references cited herein are hereby incorporated by reference in their entireties.

In the event of a conflict in a definition in the present disclosure and that of a cited reference, the present disclosure controls.

As used herein, the phrase "unacceptable level of phase separation" refers to the extent of phase separation that: (1) occurs when a sample is centrifuged at 2050 rpm in a LumiSizer 110 analytical centrifuge; and (2) is predictive of a product that possesses unacceptable physical stability.

In some embodiments, the present invention provides oral care compositions comprising a crosslinked polyvinylpyrrolidone complexed with hydrogen peroxide, and a stabilizing amount of additional linear and/or crosslinked polyvinylpyrrolidone and/or with an ethylene oxide, propylene oxide block co-polymer of formula (ethylene oxide)$_x$-(propylene oxide)$_y$ wherein x is an integer of 80-150 and y is an integer 30-80, having an average molecular weight of greater than 5000 Da. Some embodiments further comprise an abrasive. In some embodiments, the abrasive is a calcium abrasive.

Accordingly, the invention provides a dentifrice comprising (i) a crosslinked polyvinylpyrrolidone complexed with hydrogen peroxide and (ii) an ethylene oxide, propylene oxide block co-polymer of formula (ethylene oxide)$_x$-(propylene oxide)$_y$ wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800. In some embodiments, the invention provides a toothpaste comprising an abrasive, e.g., a calcium abrasive. In other embodiments, the invention provides an abrasive-free gel.

In one embodiment, the invention provides a dentifrice comprising (i) a crosslinked polyvinylpyrrolidone complexed with hydrogen peroxide and (ii) a calcium abrasive, in a dentifrice carrier.

For example, the invention provides Composition 1, a toothpaste comprising (i) a whitening complex comprising crosslinked polyvinylpyrrolidone complexed with hydrogen peroxide, (ii) a calcium abrasive, e.g.,

- 1.1. Composition 1 wherein the whitening complex contains about 10-30%, e.g., 15-25%, for example about 17-22% of hydrogen peroxide by weight, and about 5-15%, for example about 7-12% total nitrogen by weight; for example, having substantially the same specifications as Polyplasdone® XL-10, e.g., Polyplasdone® XL-10F, e.g., available from International Specialty Products (Wayne, N.J.);
- 1.2. Composition 1 or 1.1 wherein the calcium abrasive comprises a calcium phosphate salt, e.g., calcium pyrophosphate, dicalcium orthophosphate dihydrate, tricalcium phosphate, and calcium polymetaphosphate;
- 1.3. Any of the foregoing compositions wherein the calcium abrasive comprises calcium pyrophosphate;
- 1.4. Any of the foregoing compositions wherein the calcium abrasive comprises calcium carbonate;
- 1.5. Any of the foregoing compositions wherein the total amount of hydrogen peroxide by weight of the composition is 0.5-3%, e.g., 0.75-1.5%, e.g. about 1%;
- 1.6. Any of the foregoing compositions which contains less than 2% water, e.g., less than 1% water, e.g., is substantially anhydrous;
- 1.7. Any of the foregoing compositions comprising polymer thickeners selected from (i) polyethylene glycol, (ii) polyethylene glycol-polypropylene glycol block co-polymers having a molecular weight of at least 5000, and (iii) combinations thereof;
- 1.8. The preceding composition comprising an ethylene oxide, propylene oxide block co-polymer of formula (ethylene oxide)$_x$-(propylene oxide)$_y$ wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800;
- 1.9. The preceding composition additionally comprising polyethylene glycol of average molecular weight 400 to 800, e.g., about 600 Da;
- 1.10. Any of the foregoing compositions additionally comprising humectants, e.g. selected from glycerin, propylene glycol or a combination thereof;
- 1.11. Any of the foregoing compositions additionally comprising a tartar control agent, e.g., selected from tetrasodium pyrophosphate (TSPP) and sodium tripolyphosphate (STPP);
- 1.12. Any of the foregoing compositions additionally comprising a surfactant, e.g., sodium lauryl sulfate (SLS);
- 1.13. Any of the foregoing compositions additionally comprising an antibacterial agent, e.g., triclosan;
- 1.14. Any of the foregoing compositions additionally comprising an antioxidant, e.g., butylated hydoxytoluene (BHT);
- 1.15. Any of the foregoing compositions comprising any or all of the following ingredient classes and/or particular ingredients by weight:

| | |
|---|---|
| Humectants 25-40%, e.g. | |
| Glycerin | 3-7%, e.g., about 5% |
| Propylene glycol | 20-30%, e.g., about 25% |
| Thickeners, e.g. | |
| Fumed silica | 0-2%, e.g., about 1.5% |
| Polymers 10-30%, e.g., | |
| Ethylene oxide, propylene oxide block co-polymer, avg. MW >5 kDa | 5-15%, e.g., about 10% |
| Polyethylene glycol 600 | 5-15%, e.g., about 10% |
| Polyvinylpyrrolidone | 0-10% |
| Whitener, 3-10%, e.g., | |
| Crosslinked polyvinylpyrrolidone complexed with 15-25% hydrogen peroxide | 3-10%, e.g., about 5.5% |
| Abrasive, 25-45%, e.g. | |
| Calcium pyrophosphate | 25-45%, e.g., about 35% |
| Fluoride, 0-1%, e.g. | |
| Sodium monofluorophosphate | 0.5-1%, e.g., about 0.76% |
| Surfactant, e.g., SLS | 0-3% |
| Tartar control agent, e.g. TSPP | 0.5-5%, e.g., about 2% |
| Antioxidant, 0.01-5%, e.g. | |
| BHT | 0.03% |
| Flavorings | 0.1-5% |
| Water | <3% |

- 1.16. The composition resulting from the combination of the preceding ingredients.

In another embodiment, the invention provides a dentifrice comprising a crosslinked polyvinylpyrrolidone complexed with hydrogen peroxide, together with additional linear and/or crosslinked polyvinylpyrrolidone, and a dentifrice carrier.

For example, the invention provides Composition 2, a gel non-abrasive dentifrice comprising a crosslinked polyvinylpyrrolidone complexed with hydrogen peroxide, together with additional linear and/or crosslinked polyvinylpyrrolidone, e.g.,

- 2.1. Composition 1 wherein the whitening complex contains about 10-30%, e.g., 15-25%, for example about 17-22% of hydrogen peroxide by weight, and about 5-15%, for example about 7-12% total nitrogen by weight; for example, having substantially the same specifications as Polyplasdone® XL-10, e.g., Polyplasdone® XL-10F, e.g., available from International Specialty Products (Wayne, N.J.);
- 2.2. Composition 2 or 2.1 wherein the total amount of hydrogen peroxide by weight of the composition is 0.5-3%, e.g., 0.75-1.5%, e.g. about 1%;
- 2.3. Any of the foregoing compositions which contains less than 3% water, e.g., less than 1% water, e.g., is substantially anhydrous;
- 2.4. Any of the foregoing compositions comprising polymer thickeners selected from (i) polyethylene glycol, (ii) polyethylene glycol-polypropylene glycol block co-polymers having a molecular weight of at least 5000, and (iii) combinations thereof;
- 2.5. The preceding composition comprising an ethylene oxide, propylene oxide block co-polymer of formula (ethylene oxide)$_x$-(propylene oxide)$_y$ wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800;

2.6. The preceding composition additionally comprising polyethylene glycol of average molecular weight 400 to 800, e.g., about 600 Da;

2.7. Any of the foregoing compositions additionally comprising humectants, e.g. selected from glycerin, propylene glycol or a combination thereof;

2.8. Any of the foregoing compositions additionally comprising a tartar control agent, e.g., selected from tetrasodium pyrophosphate (TSPP) and sodium tripolyphosphate (STPP);

2.9. Any of the foregoing compositions additionally comprising a surfactant, e.g., sodium lauryl sulfate (SLS);

2.10. Any of the foregoing compositions additionally comprising an antibacterial agent, e.g., triclosan;

2.11. Any of the foregoing compositions additionally comprising an antioxidant, e.g., butylated hydoxytoluene (BHT);

2.12. Any of the foregoing compositions comprising any or all of the following ingredient classes and/or particular ingredients by weight:

| | |
|---|---|
| Humectants 50-70%, e.g. | |
| Glycerin | 40-55%, e.g. about 47% |
| Propylene glycol | 10-20%, e.g., about 15% |
| Fumed silica | 0-2% |
| Polymers 10-40%, e.g., | |
| Ethylene oxide, propylene oxide block co-polymer, avg. MW >5 kDa | 1-15%, e.g., about 5% |
| Polyethylene glycol 600 | 5-15%, e.g., about 10% |
| Polyvinylpyrrolidone | 1-20%, e.g., about 10% |
| Whitener, 3-10%, e.g., | |
| Crosslinked polyvinylpyrrolidone complexed with 15-25% hydrogen peroxide | 3-10%, e.g., about 5.5% |
| Fluoride, 0-1%, e.g. | |
| Sodium monofluorophosphate | 0.5-1%, e.g., about 0.76% |
| Surfactant, 0-5%, e.g | |
| SLS | 1-3%, e.g., about 2% |
| Tartar control agent, e.g. TSPP | 0.5-5%, e.g., about 2% |
| Antioxidant, 0.01-5%, e.g. | |
| BHT | 0.03% |
| Flavorings | 0.1-5% |
| Water | <3% |

2.13. The composition resulting from the combination of the preceding ingredients.

In some embodiments, the present invention provides oral care compositions comprising: a crosslinked polyvinylpyrrolidone complexed with hydrogen peroxide, a stabilizing amount of an additional linear and/or crosslinked polyvinylpyrrolidone, an abrasive and a humectant.

Some embodiments provide oral care compositions comprising: from about 0.5 to about 16.5%, by weight, crosslinked polyvinylpyrrolidone complexed with hydrogen peroxide. Other embodiments provide oral care compositions comprising: from about 1 to about 15%, by weight, crosslinked polyvinylpyrrolidone complexed with hydrogen peroxide. Still other embodiments provide oral care compositions comprising: from about 3 to about 12%, by weight, crosslinked polyvinylpyrrolidone complexed with hydrogen peroxide. Yet other embodiments provide oral care compositions comprising: from about 4 to about 10%, by weight, crosslinked polyvinylpyrrolidone complexed with hydrogen peroxide. While other embodiments provide oral care compositions comprising: from about 5 to about 8%, by weight, crosslinked polyvinylpyrrolidone complexed with hydrogen peroxide. In some embodiments, the oral care compositions comprise 5.5%, by weight, crosslinked polyvinylpyrrolidone complexed with hydrogen peroxide.

In some embodiments, the present invention provides oral care compositions comprising from about 1 to about 20% of an additional linear and/or crosslinked polyvinylpyrrolidone. Some embodiments provide compositions comprising from about 1 to about 15%, by weight, of an additional linear and/or crosslinked polyvinylpyrrolidone. Some embodiments provide compositions comprising from about 5 to about 15%, by weight, of an additional linear and/or crosslinked polyvinylpyrrolidone. Other embodiments provide compositions comprising from about 7 to about 12%, by weight, of an additional linear and/or crosslinked polyvinylpyrrolidone. Further embodiments provide oral care compositions comprising from about 8 to about 11%, by weight, of an additional linear and/or crosslinked polyvinylpyrrolidone. Still further embodiments provide compositions comprising from about 8.5 to about 10%, by weight, of an additional linear and/or crosslinked polyvinylpyrrolidone. Still other embodiments provide oral care compositions comprising 9.9% or 10%, by weight, of an additional linear and/or crosslinked polyvinylpyrrolidone. Yet other embodiments provide oral care compositions comprising about 9%, by weight, of an additional linear and/or crosslinked polyvinylpyrrolidone.

Some embodiments of the present invention provide gel-based peroxide compositions further comprise a calcium abrasive. In some embodiments, the compositions comprise from about 9 to about 25%, by weight, propylene glycol. In some embodiments, the compositions comprise from about 14 to about 32%, by weight, glycerin. In other embodiments, the compositions comprise less than 20%, by weight, of a calcium abrasive. Some embodiments provide compositions comprising from about 9 to about 25%, by weight, propylene glycol; from about 14 to about 32%, by weight, glycerin; and less than 20%, by weight, of a calcium abrasive.

Still other embodiments provide oral care compositions comprising from about 20 to about 60%, by weight, humectant.

Yet further embodiments provide oral care compositions comprising from about 5 to about 15%, by weight, abrasive.

The compositions of the invention a "low water" content, meaning that a total concentration of water, including any free water and all water contained in any ingredients, is less than about 5%, preferably less than 3%, preferably less than 2% water.

Where abrasives are present, the average particle size is generally about 0.1 to about 30 microns, for example about 1 to about 20 or about 5 to about 15 microns.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The anticalculus agent is present at about 0.1% to about 30%. The oral composition may include a mixture of different anticalculus agents. In one preferred embodiment, tetrasodium pyrophosphate (TSPP) and sodium tripolyphosphate (STPP)

are used. The anticalculus agent comprises TSPP at about 1-2% and STPP at about 7% to about 10%.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions.

The compositions of the invention may also comprise various dentifrice ingredients to adjust the rheology and feel of the composition such as humectants, surface active agents, thickening or gelling agents, etc.

The compositions of the present invention may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

The compositions of the present invention optionally comprise a thickener. Any orally acceptable thickening agent can be used, including without limitation carbomers, also known as carboxyvinyl polymers, carrageenans, also known as Irish moss and more particularly—carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

In various preferred embodiments, the carrier may comprise polymers and/or copolymers of polyethylene glycol, of ethylene oxide/propylene oxide, and of silicone. If such copolymers/polymers are used, they may be selected from commercially available materials. Block copolymers of ethylene oxide/propylene oxide are useful, but higher molecular weight, e.g., >5000 Da are preferred, e.g. including PLURACARE® L1220 (available from BASF, Wyandotte, Mich., United States of America). Low or medium molecular weight polyethylene glycol, e.g., PEG 400, PEG 600, PEG 800, PEG 1000 and mixtures thereof are also useful. It is preferred that the carrier(s) provide a dentifrice with a viscosity of about 10,000 CPS to about 700,000 CPS, preferably about 30,000 CPS to about 300,000 CPS.

As recognized by one of skill in the art, the oral compositions of the present invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention optionally comprise one or more further active material(s), which is operable for the prevention or treatment of a condition or disorder of hard or soft tissue of the oral cavity, the prevention or treatment of a physiological disorder or condition, or to provide a cosmetic benefit.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The compositions of the present invention optionally comprise an antimicrobial (e.g., antibacterial) agent. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3%.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a sialagogue or saliva-stimulating agent, an antiplaque agent, an anti-inflammatory agent, and/or a desensitizing agent.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouthfeel, taste, odor and so forth.

Methods are provided to whiten an oral surface in a human or animal subject comprising storing in stable form a composition of the invention, e.g., Composition 1, et seq. or Composition 2, et seq. as described above, and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the peroxide incompatible abrasive, and other ingredients.

In various embodiments, it is preferred that the oral care composition is applied and contacted with the oral surface. The dentifrice, prepared in accordance with the present invention is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

In some embodiments, the diameter of the top of the tube in which the a composition of the present invention is packaged, expands less than 0.1 cm, after 1 week of aging at 60° C. In some embodiments, the diameter of the top of the tube in an oral care composition of the present invention is packaged, expands less than 0.05 cm, after 1 week of aging at 60° C. In other embodiments, the diameter of the top of the tube in which a composition of the present invention is packaged, expands less than 0.04 cm, after 1 week of aging at 60° C. In further embodiments, the diameter of the top of the tube in which a composition of the present invention is packaged, expands less than 0.03 cm, after 1 week of aging at 60° C. In other embodiments, the diameter of the top of the tube in which a composition of the present invention is packaged, expands less than 0.02 cm, after 1 week of aging at 60° C. In yet other embodiments, the diameter of the top of the tube in which a composition of the present invention is packaged, expands less than 0.01 cm, after 1 week of aging at 60° C. While in other embodiments, the diameter of the top of the tube in which a composition of the present invention is packaged, does not expand to a measurable extent.

In some embodiments, the compositions of the present invention do not exhibit an unacceptable level of phase separation after 30 minutes at 2050 rpm in a LumiSizer 110 analytical centrifuge. In other embodiments, the compositions of the present invention do not exhibit an unacceptable level of phase separation after 35 minutes at 2050 rpm in a LumiSizer 110 analytical centrifuge. In further embodiments, the compositions of the present invention do not exhibit an unacceptable level of phase separation after 40 minutes at 2050 rpm in a LumiSizer 110 analytical centrifuge. In still further embodiments, the compositions of the present invention do not exhibit an unacceptable level of phase separation after 45 minutes at 2050 rpm in a LumiSizer 110 analytical centrifuge. In yet other embodiments, the compositions of the present invention do not exhibit an unacceptable level of phase separation after 50 minutes at 2050 rpm in a LumiSizer 110 analytical centrifuge. In some embodiments, the compositions of the present invention do not exhibit an unacceptable level of phase separation after 55 minutes at 2050 rpm in a LumiSizer 110 analytical centrifuge. Still other embodiments provide compositions that do not exhibit an unacceptable level of phase separation after 60 minutes at 2050 rpm in a LumiSizer 110 analytical centrifuge. While other embodiments provide compositions that do not exhibit an unacceptable level of phase separation after 65 minutes at 2050 rpm in a LumiSizer 110 analytical centrifuge. In some embodiments, the compositions of the present invention do not exhibit an unacceptable level of phase separation after 70 minutes at 2050 rpm in a LumiSizer 110 analytical centrifuge. In some embodiments, the compositions of the present invention do not exhibit an unacceptable level of phase separation after 75 minutes at 2050 rpm in a LumiSizer 110 analytical centrifuge. In some embodiments, the compositions of the present invention do not exhibit an unacceptable level of phase separation after 80 minutes at 2050 rpm in a LumiSizer 110 analytical centrifuge. In some embodiments, the compositions of the present invention do not exhibit an unacceptable level of phase separation after 85 minutes at 2050 rpm in a LumiSizer 110 analytical centrifuge. In some embodiments, the compositions of the present invention do not exhibit an unacceptable level of phase separation after 90 minutes at 2050 rpm in a LumiSizer 110 analytical centrifuge. In some embodiments, the compositions of the present invention do not exhibit an unacceptable level of phase separation after 95 minutes at 2050 rpm in a LumiSizer 110 analytical centrifuge. In some embodiments, the compositions of the present invention do not exhibit an unacceptable level of phase separation after 100 minutes at 2050 rpm in a LumiSizer 110 analytical centrifuge. In some embodiments, the compositions of the present invention do not exhibit an unacceptable level of phase separation after 105 minutes at 2050 rpm in a LumiSizer 110 analytical centrifuge. In some embodiments, the compositions of the present invention do not exhibit an unacceptable level of phase separation after 110 minutes at 2050 rpm in a LumiSizer 110 analytical centrifuge. In some embodiments, the compositions of the present invention do not exhibit an unacceptable level of phase separation after 115 minutes at 2050 rpm in a LumiSizer 110 analytical centrifuge. In some embodiments, the compositions of the present invention do not exhibit an unacceptable level of phase separation after 120 minutes at 2050 rpm in a LumiSizer 110 analytical centrifuge. In some embodiments, the compositions of the present invention do not exhibit an unacceptable level of phase separation after 125 minutes at 2050 rpm in a LumiSizer 110 analytical centrifuge.

In some embodiments, the diameter of the top of the tube in which a composition of the present invention is packaged, expands less than 0.01% of the top diameter of the tube, after 1 week of aging at 60° C. In some embodiments, the diameter of the top of the tube in which a composition of the present invention is packaged, expands less than 0.05% of the top diameter of the tube, after 1 week of aging at 60° C. In some embodiments, the diameter of the top of the tube in which a composition of the present invention is packaged, expands less than 0.1% of the top diameter of the tube, after 1 week of aging at 60° C. In some embodiments, the diameter of the top of the tube in which a composition of the present invention is packaged, expands less than 0.5% of the top diameter of the tube, after 1 week of aging at 60° C. In some embodiments, the diameter of the top of the tube in which a composition of the present invention is packaged, expands less than 1% of the top diameter of the tube, after 1 week of aging at 60° C. In some embodiments, the diameter of the top of the tube in which a composition of the present invention is packaged, expands less than 3% of the top diameter of the tube, after 1 week of aging at 60° C. In some embodiments, the diameter of the top of the tube in which a composition of the present invention is packaged, expands less than 5% of the top diameter of the tube, after 1 week of aging at 60° C. In some embodiments, the diameter of the top of the tube in which a composition of the present invention is packaged, expands less than 10% of the top diameter of the tube, after 1 week of aging at 60° C. In some embodiments, the diameter of the top of the tube in which a composition of the present invention is packaged, expands less than 15% of the top diameter of the tube, after 1 week of aging at 60° C. In some embodiments, the diameter of the top of the tube in which a composition of the present invention is packaged, expands less than 20% of the top diameter of the tube, after 1 week of aging at 60° C.

In some embodiments, the diameter of the top of the tube in which a composition of the present invention is packaged, expands less than 25% of the top diameter of the tube, after 1 week of aging at 60° C. In other embodiments, the diameter of the top of the tube in which a composition of the present invention is packaged, expands less than 30% of the top diameter of the tube, after 1 week of aging at 60° C. In some embodiments, the diameter of the top of the tube in which a composition of the present invention is packaged, expands less than 35% of the top diameter of the tube, after 1 week of aging at 60° C. In some embodiments, the diameter of the top of the tube in which a composition of the present invention is packaged, expands less than 40% of the top diameter of the tube, after 1 week of aging at 60° C. In some embodiments, the diameter of the top of the tube in which a composition of the present invention is packaged, expands less than 45% of the top diameter of the tube, after 1 week of aging at 60° C. In some embodiments, the diameter of the top of the tube in which a composition of the present invention is packaged, expands less than 50% of the top diameter of the tube, after 1 week of aging at 60° C.

The invention is illustrated in the following non-limiting examples.

EXAMPLES

Example 1

A gel dentifrice having a peroxide composition of about 1% is prepared having the following ingredients:

TABLE 1

| Ingredient | % (w/w) |
|---|---|
| 85% syrupy phosphoric acid | 0.2 |
| $PEG_{118}/PPG_{66}$ co-polymer | 5 |
| Glycerin | 47 |
| Propylene glycol | 15 |
| PEG 600 | 10 |
| PVP | 10 |
| Crosslinked $PVP/H_2O_2$ | 5.5 |
| TSPP | 2 |
| Sucralose | 0.05 |
| Sodium saccharine | 0.6 |
| Sodium monofluorophosphate | 0.76 |
| Sodium lauryl sulfate | 2 |
| BHT | 0.03 |
| Mint flavor | 2 |

Example 2

A gel dentifrice having a peroxide composition of about 1% is prepared having the following ingredients:

TABLE 2

| Ingredient | % (w/w) |
|---|---|
| 85% syrupy phosphoric acid | 0.2 |
| Glycerin | 25.36 |
| $PEG_{118}/PPG_{66}$ co-polymer | 7.5 |
| PEG 600 | 10 |
| Propylene glycol | 25 |
| Crosslinked $PVP/H_2O_2$ | 5.5 |
| TSPP | 2 |
| Sucralose | 0.05 |
| Sodium saccharin | 0.6 |
| Sodium monofluorophosphate | 0.76 |
| Calcium pyrophosphate | 10 |
| PVP | 9 |
| BHT | 0.03 |
| Flavor | 2 |
| Sucralose | 0.05 |
| Sodium lauryl sulfate | 2 |

Example 3

A toothpaste having a peroxide content of about 1% is prepared with the following ingredients:

TABLE 3

| Ingredient | % (w/w) |
|---|---|
| 85% syrupy phosphoric acid | 0.2 |
| $PEG_{118}/PPG_{66}$ co-polymer | 10 |
| Glycerin | 5 |
| PEG 600 | 10 |
| Propylene glycol | 25 |
| Crosslinked $PVP/H_2O_2$ | 5.5 |
| TSPP | 2 |
| Sucralose | 0.05 |
| Sodium saccharine | 0.6 |
| Sodium monofluorophosphate | 0.76 |
| Calcium pyrophosphate | 35 |
| Fumed silica | 1.5 |
| BHT | 0.03 |
| Mint flavor | 2.25 |

Example 4

The in vitro whitening efficacy of the compositions of Examples 1 and 3 are tested versus commercial whitening dentifrices.

Brushing Test:

The in vitro whitening efficacy of the products is tested by brushing experiments. Bovine teeth are prophy stained to achieve similar initial lightness values. The bovine teeth are mounted in a tray for brushing study. A 1:1 slurry of dentifrice to deionized water is prepared and 25 grams added to brushing tray. The stained bovine teeth are brushed for 20 minutes at 120 strokes/min. This is intended to approximate one week of bushing (1.5 min brushing, twice a day for seven days=21 minutes/week). Teeth are rinsed with 100 g deionized water, then the color (L*a*b* values) is measured with a spectrophotometer. This is repeated three times.

The spectrophotometer used is Spectroshade from MHT. The measurement scale is the CIE L*a*b* (CIELAB) scale developed by the International Commission on Illumination (CIE). CIELAB is an opponent color system based on the fact that retinal color stimuli are translated into distinctions between light and dark, red and green, and blue and yellow. CIELAB indicates these values with three axes: L*, a*, and b*. The L value indicates the lightness of a color, where L=0 is black and L=100 is white. $\Delta L = L_{brushed} - L_{initial}$. Thus, a larger positive ΔL value=whiter teeth. The a value ranges between +a=magenta and −a=green. The b value ranges between +b=yellow and −b=blue. The W value incorporates the L, a and b values to describe how close the measured color is to true white, where W*=(a2+b2+(L*−100)2)½. A larger negative ΔW value corresponds to greater whitening.

In comparing the toothpaste formulation of Example 3 with a leading commercial whitening toothpaste (Brand A), the formulation of Example 3 shows significantly greater whitening:

TABLE 4

| ΔL using Brand A and Example 3: | | | | |
|---|---|---|---|---|
| | 20 mins | 40 mins | 60 mins | 80 mins |
| Brand A | 2.1 + 0.6 | 3.1 + 0.7 | 3.6 + 0.6 | 3.8 + 1.0 |
| Example 3 | 4.4 + 0.9 | 5.4 + 0.9 | 6.5 + 1.0 | 7.5 + 0.9 |

TABLE 5

| ΔW using Brand A and Example 3: | | | | |
|---|---|---|---|---|
| | 20 mins | 40 mins | 60 mins | 80 mins |
| Brand A | −2.2 + 0.5 | −3.1 + 0.6 | −3.5 + 0.4 | −3.6 + 0.9 |
| Example 3 | −4.0 + 0.9 | −4.8 + 1.4 | −6.1 + 1.6 | −7.0 + 1.3 |

Similar results are obtained with the gel of Example 1. After four cycles of brushing (80 minutes), the ΔL and ΔW are as follows:

TABLE 6

| ΔL and ΔW using Brand A and Example 1 | | |
|---|---|---|
| | ΔL | ΔW |
| Brand A | 3.8 + 1.0 | −3.6 + 0.9 |
| Example 1 | 7.3 + 2.6 | −6.0 + 2.8 |

Bleaching Test:

Hard abrasive particles serve to break up the stain during the act of brushing when they are rubbed against the stain by the bristles of the toothbrush. Peroxide whitens both extrinsic (surface stains) and intrinsic stains (below the surface of enamel) through a chemical reaction in which the unsaturated bonds in colored stain molecules are oxidized by peroxide to become colorless. In this test method stained hydroxyapatite disks are soaked in dentifrice slurry. As disks are soaked, rather than brushed, stains will be bleached by toothpaste containing peroxide but should not be removed by toothpastes containing only abrasives. The substrate used is 1" diameter hydroxyapatite (HAP) disks (human enamel is ~96% hydroxyapatite by weight; human dentin is ~70% hydroxyapatite by weight). The HAP are stained using a mixture of common foods that stain teeth: 1 part 1% instant coffee solution (Maxwell House), 1 part brewed black tea (Lipton Black Tea soaked for 2 min in hot water), 1 part red wine (Cabernet). The HAP disks are soaked overnight in artificial saliva. The saliva treated disks are soaked in staining solution for 2 hrs, rinsed with water, and dried. The disks are then soaked in a stirring dentifrice slurry for 2 min, rinsed with water and dried.

TABLE 7

| ΔW using Brand A and Example 1 in bleaching test; stained HAP disks soaked in 1:2 dentifrice to water slurry for 2 min | | | | | |
|---|---|---|---|---|---|
| | L | a | b | W* | ΔW |
| Control | 80.17 | 5.51 | 6.18 | 21.49 | |
| Brand A | 85.79 | 3.02 | 4.24 | 15.13 | −6.36 |
| Example 1 | 95.43 | 0.07 | 1.61 | 4.85 | −16.64 |

Example 1 is then further tested versus a commercially available 1% peroxide toothpaste (Brand B).

TABLE 8

| ΔW for Example 1 versus Brand B in a bleaching test; stained HAP disks soaked in a 1:1 dentifrice to water slurry for 2 minutes. | | | | | |
|---|---|---|---|---|---|
| | L | a | b | W* | ΔW |
| Control | 79.59 | 5.52 | 6.43 | 22.10 | |
| Example 1 | 96.61 | −.31 | 1.37 | 3.67 | −18.43 |
| Brand B | 96.36 | −.91 | 3.45 | 5.10 | −17.00 |

The data described in Table 8 indicates that an exemplary composition of the present invention provides a significant improvement in ΔW over a commercially available 1% peroxide toothpaste.

Example 5

The objective of the consumer test is to determine how the two test formulas with peroxide compare in consumer preference and whitening performance after 2 weeks of use vs. the leading peroxide and nonperoxide competition.

Two Week Results: Both Examples 1 and 3 deliver higher % of noticeable whitening amongst consumers who perceived their teeth to be whiter vs. Brand A after 1 week of use [71% for Example 1 (1% gel), 77% for Example 3 (1% paste), 58% for Brand A]. Also two statements come up higher for both Examples than for Brand A: “This toothpaste gives me 360 degree coverage for an all over white” and “This toothpaste is the most convenient way to get noticeably whiter teeth in just 1 week”. Both Examples were significantly better than Brand B in overall and taste liking.

Example 6

The toothpaste of Example 3 is tested for stability versus a commercially available 1% peroxide toothpaste. Peroxide-containing compositions which bloat to an unacceptable extent would not be expected to provide the level of whitening suitable for a toothpaste composition.

Tube Bloating:

The diameter of the tube is measured at the bottom (close to cap), the midpoint, and the top (close to crimp), before and after 1 week of aging at 60° C. The elevated temperature accelerates the aging, approximating the degree of degradation that can be expected to occur over long-term storage at room temperature.

TABLE 9

| | Top | | Middle | | Bottom | |
|---|---|---|---|---|---|---|
| | Set 1 (change in cm) | Set 2 (change in cm) | Set 1 (change in cm) | Set 2 (change in cm) | Set 1 (change in cm) | Set 2 (change in cm) |
| Example 3 | 0.02 | 0.00 | 0.20 | 0.10 | 0.10 | −0.20 |
| Brand B | 0.10 | 0.20 | 0.10 | 0.20 | −0.10 | 0.20 |

Physical Separation:

Samples are centrifuged using an analytical centrifuge (LumiSizer 110 from L.U.M. GmbH, Berlin), which measures separation of the product by measuring optical transmission through the tube as a function of time.

The results show that it takes longer for Example 3 to separate than Brand B:

TABLE 10

| Sample | Example 3 | Brand B |
|---|---|---|
| Time to Separation at 2050 rpm (mins) | 133 ± 5 | 40 ± 10 |

Example 7

Bloating Study:

a bloating study was also conducted on gel based abrasive containing compositions of the present invention to evaluate their chemical stability profiles. Unexpectedly, the gel based abrasive containing compositions of the present invention which comprise from about 9 to about 25%, by weight, propylene glycol; from about 14 to about 32%, by weight, glycerin; and from about 1 to about 15%, by weight, of an additional linear and/or crosslinked polyvinylpyrrolidone, do not bloat to an unacceptable extent after 1 week of aging at 60° C.

The data described in the Examples evidences the unexpected improvement in chemical and physical stability demonstrated by compositions of the present invention.

While particular embodiments of the present invention have been illustrated and described, it will be obvious to those skilled in the art that various changes and modifications may be made without departing from the spirit and scope of the invention. It is therefore intended to cover in the appended claims all such changes and modifications which are within the scope of the invention.

The invention claimed is:

1. A gel non-abrasive dentifrice composition comprising (i) a whitening complex of crosslinked polyvinylpyrrolidone complexed with hydrogen peroxide, wherein the whitening complex contains about 10-30% hydrogen peroxide, by weight, and about 5-15% total nitrogen by weight, and (ii) additional linear polyvinyl pyrrolidone and/or cross-linked polyvinylpyrrolidone;

(iii) 10-20% by weight propylene glycol and 40-55% by weight glycerin;

(iv) 5-15% by weight of polyethylene glycol of average molecular weight 400 to 800 Da;

(v) sodium monofluorophosphate present in an amount providing 200 to 5000 ppm of fluoride ions;

(vi) sodium lauryl sulfate;

and wherein the composition comprises 0.5 to 3% of total hydrogen peroxide by weight of the composition, and wherein the composition comprising less than 3% by weight of water.

2. The composition of claim 1 wherein the composition comprises from 1 to 20% by weight of the additional linear and/or cross-linked polyvinylpyrrolidone.

3. The composition of claim 1 wherein the additional linear and/or cross-linked polyvinylpyrrolidone is cross-linked polyvinylpyrrolidone.

4. The composition of claim 1, wherein the composition further comprises a tartar control agent selected from tetrasodium pyrophosphate, sodium tripolyphosphate and mixtures thereof.

5. The composition of claim 1, wherein the composition comprises from 5 to 15% by weight of the additional linear and/or cross-linked polyvinylpyrrolidone.

6. The composition of claim 1, wherein the composition comprises from 8 to 11% by weight of the additional linear and/or cross-linked polyvinylpyrrolidone.

7. The composition of claim 1, further comprising one or more thickeners selected from the group consisting of carbomers, carrageenans, cellulosic polymers, and natural gums, wherein the thickeners are present in a total amount of 5 to 35% by weight of the composition.

8. The composition of claim 7, wherein the thickener comprises hydroxyethyl cellulose, carboxymethyl cellulose or xanthan gum.

9. The composition of claim 1, further comprising a stannous ion source in an amount of 0.1 to 7% by weight of the composition.

10. The composition of claim 1, wherein the stannous ion source is stannous fluoride.

11. The composition according claim 1, wherein the sodium monofluorophosphate is present in an amount of 0.5 to 1% by weight.

* * * * *